US00PP27892P3

(12) United States Plant Patent
Randag

(10) Patent No.: US PP27,892 P3
(45) Date of Patent: Apr. 11, 2017

(54) CALLA LILY PLANT NAMED 'SUMMER SUN'

(50) Latin Name: *Zantedeschia sprengeri*
Varietal Denomination: Summer Sun

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 44 days.

(21) Appl. No.: 14/544,321

(22) Filed: Dec. 22, 2014

(65) Prior Publication Data

US 2015/0296686 P1 Oct. 15, 2015

Related U.S. Application Data

(60) Provisional application No. 61/964,771, filed on Jan. 14, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; May 19, 2016; cultivar name—'Summer Sun' (1 pg).*

* cited by examiner

*Primary Examiner* — Susan McCormick Ewoldt
(74) *Attorney, Agent, or Firm* — The Webb Law Firm

(57) ABSTRACT

'Summer Sun' is a new variety of calla lily having inflorescences with a yellow-colored spathe that produces 5-20 inflorescences per tuber. The inflorescence stems are about 35 cm in height, and the leaves are green with whitish spots and have a leathery texture.

2 Drawing Sheets

Botanical classification: *Zantedeschia sprengeri*.
Varietal denomination: 'SUMMER SUN'.

BACKGROUND OF THE NEW PLANT

The present invention comprises a new and distinct cultivar of calla lily, botanically known as *Zantedeschia sprengeri* and hereinafter referred to by the cultivar name 'Summer Sun'.

'Summer Sun' is a product of a planned breeding program which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* 'Red Sox' (female parent, U.S. Plant Pat. No. 14,063) with *Zantedeschia sprengeri* 'Sunglow' (male parent, unpatented). 'Summer Sun' was selected in 2004 by the inventor in 't Zand, The Netherlands as one flowering plant within the progeny of the stated cross.

The first act of asexual reproduction of 'Summer Sun' by tissue culture was performed by the inventor in September of 2007 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Summer Sun' which, in combination, distinguish this calla lily as a new and distinct cultivar:

1. Yellow-colored spathe having a pink blush;
2. Green-colored leaves with numerous white-colored and linear spots; and
3. High inflorescence production.

Further, when compared to calla lily plant named 'Yellow Jacket BLZ' (U.S. Plant Pat. No. 20,217, the upper surface spathe color of 'Yellow Jacket BLZ' is Yellow Group RHS 7A and the lower surface spathe color of 'Yellow Jacket BLZ' is Yellow Group RHS 7B, whereas the upper and lower surface spathe color of 'Summer Sun' varies between Yellow Group RHS 9A to 9B.

Table 1 provides similarities and differences of 'Summer Sun' to its parents, *Zantedeschia sprengeri* varieties 'Red Sox' and 'Sunglow'.

TABLE 1

| 'Summer Sun' | Similarities | Differences |
|---|---|---|
| 'Red Sox' | Plant height | Spathe color (Varies between Greyed-Purple Group RHS 182A to 184A)<br>Number of inflorescences (1-4)<br>Spathe shape (Between funnel and cupped) |
| 'Sunglow' | Number of inflorescences | Spathe shape (Funnel)<br>Plant height (10-30 cm)<br>Spathe color (Reddish-orange in color, RHS values unknown) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
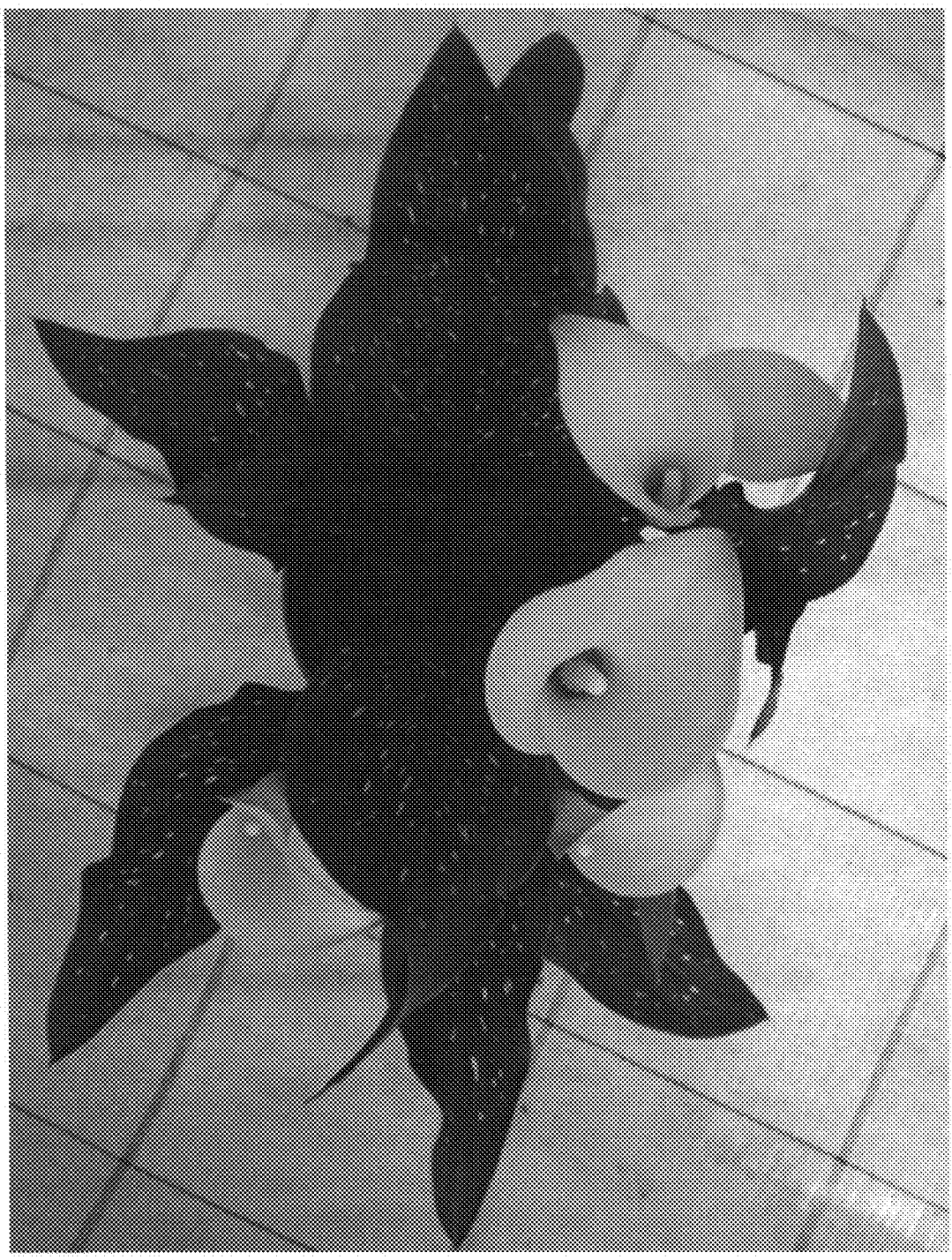
FIG. 1 is a photograph of an overhead view of the new variety.
Figure 2:
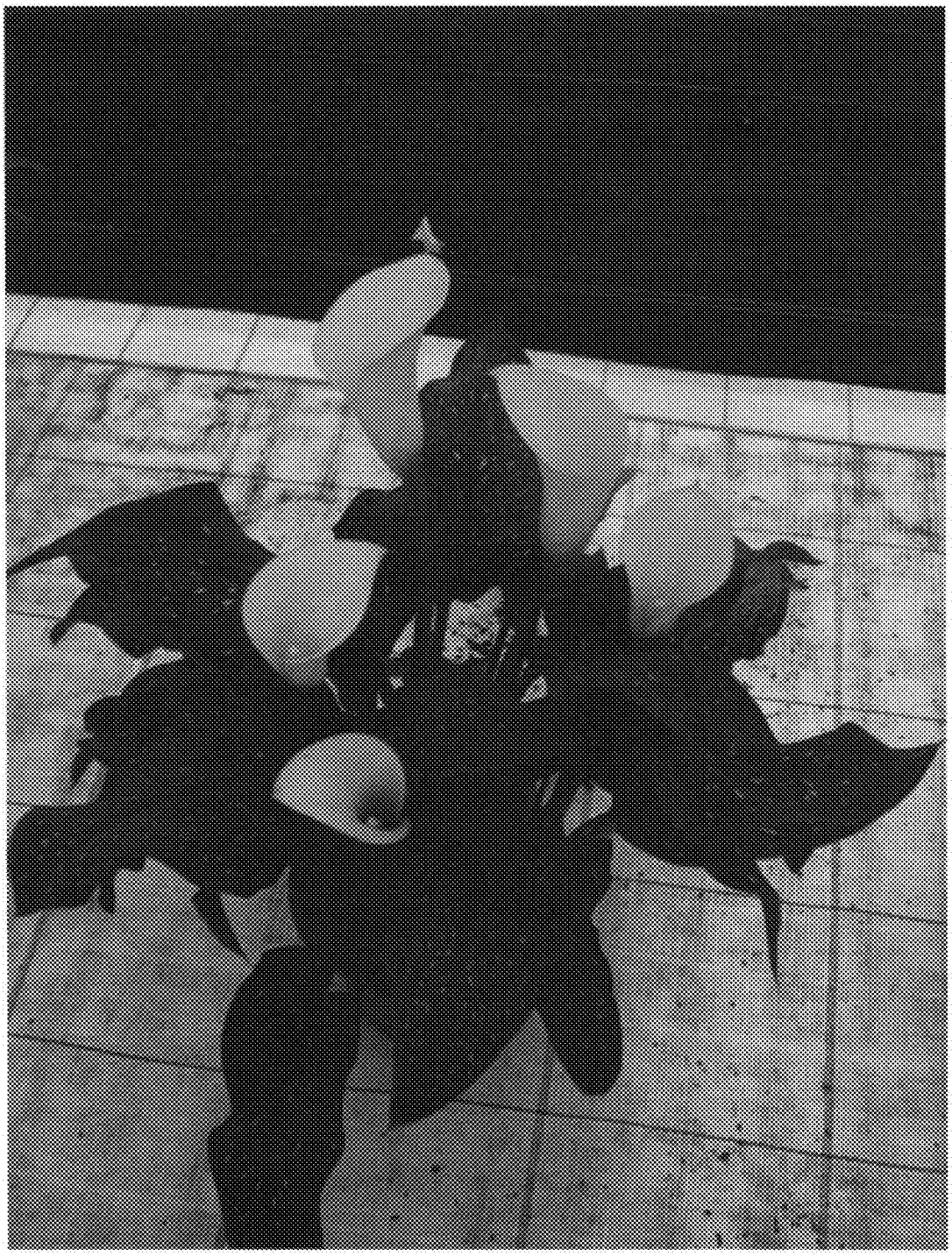
FIG. 2 is a photograph of a side view of the new variety

Size:

*Height of the leaf canopy above the soil.*—10-40 cm.

*Height of top of inflorescence above the soil.*—10-40 cm.

*Diameter.*—20-40 cm.

Form: Erect.

Number of inflorescences per tuber:

*Size* 14-16 *cm in diameter.*—5-7 inflorescences.

*Size* 16-18 *cm in diameter.*—6-12 inflorescences.

*Size* 18-20 *cm in diameter.*—7-20 inflorescences.

Branches:

*Character.*—Many (from 3-8); like the variety 'Odessa' (U.S. Plant Pat. No. 18,833.

*Color.*—Between Green Group RHS 137A and 137B.

Leaves:

*Size.*—Width: 4.5-13 cm. Length: 12-24 cm.

*Number per plant.*—20-35.

*Shape.*—Lanceolate.

*Color.*—Upper surface: Green Group RHS 137A to Greyed-Green Group RHS 189A, with transparent White Group RHS 155A and N155A spots. Lower surface: Green Group RHS 137A to 137C, with transparent White Group RHS 155A and N155A spots.

*Apex.*—Acuminate.

*Base.*—Truncate.

*Margin.*—Undulate; having a color of Green Group RHS 137A to Greyed-Green Group RHS 189A.

*Veins.*—Configuration: Pinnate. Color: Green Group RHS 137C to 137D.

*Surface quality.*—Leathery.

*Petiole.*—Length: 7-25 cm. Diameter: 8 mm. Color: The base is White Group RHS 155A, and the upper part is Yellow-Green Group RHS 144A to 144B.

Roots:

*Color.*—White.

*Branching.*—Similar to other *Zantedeschia* varieties.

The Inflorescence and Seeds

Spathe:

*Size.*—Length (measured from base opening to tip): 4-8 cm. Width: 3-6 cm. Height: 4-8 cm.

*Color.*—Upper surface: Varies between Yellow Group RHS 9A to 9B. Lower surface: Varies between Yellow Group RHS 9A to 9B.

*Vein color.*—Between Yellow Group RHS 9A to 9B.

*Shape.*—Cupped.

*Apex.*—Apiculate.

*Base.*—Obtuse.

*Texture.*—Smooth (upper and lower surfaces).

Spadix:

*Size.*—Length: 30-45 mm. Diameter: 3-8 mm.

*Color.*—Between Yellow-Orange Group RHS 17A and 17B.

*Position relative to spathe.*—Upright.

Peduncle:

*Size.*—Length: 10-35 cm. Diameter: 4-11 mm.

*Color.*—The upper part is between Yellow-Green Group RHS 144A and 144B, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow-Orange Group RHS 17A and 17B.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 13B and 13C.

*Ovaries.*—Texture: Smooth. Length: Between 1 to 10 mm. Width: Between 1 to 10 mm. Color: Top color is between Yellow-Green Group RHS 150C and 150D, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-50.

Fruit:

*Amount.*—Multiple berries produced.

*Shape.*—Irregular.

*Color*.—Varies between Green Group RHS N143A to 145C.

General

Disease resistance: No unusual susceptibility to diseases noticed to date.
Pest resistance: No unusual susceptibility to pests noticed to date.
Heat tolerance: No heat tolerance.
Hardiness: Not hardy.
Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.
Lastingness: About two weeks on the plant.
Fragrance: None.

I claim:

1. A new and distinct variety of calla lily plant named 'Summer Sun' as herein described and illustrated.

* * * * *